(12) United States Patent
Picard et al.

(10) Patent No.: US 9,393,290 B2
(45) Date of Patent: *Jul. 19, 2016

(54) COMBINATION THERAPY FOR TREATMENT OF PATIENTS WITH NEUROLOGICAL DISORDERS AND CEREBRAL INFARCTION

(71) Applicant: MOLEAC PTE. LTD., Singapore (SG)

(72) Inventors: David Picard, Singapore (SG); Xue Min Shi, Tianjin (CN); Michael Lazdunski, Nice (FR)

(73) Assignee: MOLEAC PTE. LTD., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 14/476,534

(22) Filed: Sep. 3, 2014

(65) Prior Publication Data

US 2014/0369995 A1   Dec. 18, 2014

Related U.S. Application Data

(63) Continuation of application No. 13/128,529, filed as application No. PCT/SG2009/000416 on Nov. 10, 2009, now Pat. No. 8,852,578.

(30) Foreign Application Priority Data

Nov. 10, 2008   (SG) ............................... 200808340-4

(51) Int. Cl.
*A61K 36/00* (2006.01)
*A61K 38/48* (2006.01)
*A61K 35/36* (2015.01)
(Continued)

(52) U.S. Cl.
CPC ............... *A61K 38/482* (2013.01); *A61K 35/36* (2013.01); *A61K 35/413* (2013.01); *A61K 35/62* (2013.01); *A61K 35/64* (2013.01); *A61K 35/646* (2013.01); *A61K 36/232* (2013.01); *A61K 36/481* (2013.01); *A61K 36/537* (2013.01); *A61K 36/65* (2013.01); *A61K 36/69* (2013.01); *A61K 36/88* (2013.01); *A61K 45/06* (2013.01); *A61K 38/00* (2013.01)

(58) Field of Classification Search
CPC . A61K 36/232; A61K 36/481; A61K 36/236; A61K 36/69
See application file for complete search history.

(56) References Cited

U.S. PATENT DOCUMENTS

| 5,942,233 | A | 8/1999 | Chang |
| 2003/0211178 | A1 | 11/2003 | Xia |
| 2007/0059386 | A1 | 3/2007 | Lee |

FOREIGN PATENT DOCUMENTS

| CN | 1435242 A | 8/2003 |
| CN | 1485077 A | 3/2004 |

(Continued)

OTHER PUBLICATIONS

Gan, R. et al., "Danqi Piantan Jiaonang Does Not Modify Hemostasis, Hematology, and Biochemistry in Normal Subjects and Stroke Patients," *Cerebrovascular Diease* 25:450-456 (2008).

Hua Chiang Siow, C., "Neuroaid in Stroke Recovery," *European Neurology* 60:264-266 (2008).

International Preliminary Report on Patentability for PCT/SG2009/000416 dated Jan. 18, 2011.

(Continued)

*Primary Examiner* — Rosanne Kosson
(74) *Attorney, Agent, or Firm* — Marshall, Gerstein & Borun LLP (57) ABSTRACT

The present invention provides compositions and methods for treating stroke patients using TCM and a Western medicament used for the treatment of stroke patients.

20 Claims, 3 Drawing Sheets

(51) Int. Cl.
- *A61K 35/62* (2006.01)
- *A61K 45/06* (2006.01)
- *A61K 35/413* (2015.01)
- *A61K 35/646* (2015.01)
- *A61K 36/232* (2006.01)
- *A61K 36/88* (2006.01)
- *A61K 36/481* (2006.01)
- *A61K 36/537* (2006.01)
- *A61K 36/65* (2006.01)
- *A61K 36/69* (2006.01)
- *A61K 35/64* (2015.01)
- *A61K 38/00* (2006.01)

(56) References Cited

FOREIGN PATENT DOCUMENTS

| | | |
|---|---|---|
| CN | 1726966 A | 2/2006 |
| CN | 1973865 A | 6/2007 |
| CN | 101088532 A | 12/2007 |
| CN | 101194939 A | 6/2008 |
| CN | 101244206 A | 8/2008 |
| WO | WO-2007/106049 A1 | 9/2007 |

OTHER PUBLICATIONS

International Search Report for PCT/SG2009/000416 dated Jan. 19, 2010.

COMBINATION THERAPY FOR TREATMENT OF PATIENTS WITH NEUROLOGICAL DISORDERS AND CEREBRAL INFARCTION

FIELD OF THE INVENTION

The present invention provides methods and compositions for the treatment of stroke and neurological disorders. The methods and compositions of the present invention bring together aspects of Traditional Chinese Medicine (TCM) and Western medicine.

BACKGROUND

Stroke is a major cause of death and disability. Primary stroke prevention focuses on lifestyle modifications of risk factors while secondary stroke prevention aims to reduce the overall risk of recurrence in persons who have had a stroke.

There is currently a lack of treatment methods for stroke recovery in Western medicine, these being frequently limited to the following options:
  a) Intra-arterial thrombolysis with intravenous tissue plasminogen activator (rt-PA), which is applicable only to 3 to 5% of stroke patients (as it has to be applied only for acute ischemic forms, only if patients do not present any contra-indication, and only within 3 to 6 hours after the onset of symptoms), can restore blood perfusion and prevent neurological and functional damage to some degree;
  b) administration of aspirin/other antiplatelets/or sometimes anticoagulant to most of the cerebral stroke patients for secondary stroke prevention, which gives an improvement effect of about 1% (The International Stroke Trial (IST) a randomised trial of aspirin, subcutaneous heparin, both or neither among 19435 patients with acute ischaemic stroke. International Stroke Trial Collaborative Group. Lancet. 1997 May 31; 349(9065): 1569-81);
  c) medications such as analgesics may be needed to control associated symptoms
  d) rehabilitation includes physical therapy such as physiotherapy, massage, speech therapy, or occupational therapy.

One known TCM product is NeuroAid®. Clinical studies performed in China on compositions the same as NeuroAid® have shown that this natural product combination increases stroke patients' neurological disability recovery and functional outcomes with extremely few side effects or other adverse effects. The composition of NeuroAid® has been approved by and registered with the State Food and Drug Administration (SFDA) and is administered for the treatment of cerebral infarct patients during their recovery at an early or late stage, and the indications in Traditional Chinese Medicine are: to supplement qi and activate blood circulation. It is applied to treat those patients who are suffering from ischemic or hemorrhagic (for the latter, it is at present indicated in late phase only) cerebral infarction of qi deficiency and blood stasis with manifestations of hemiplegia, hemianesthesia, wry mouth, aphasia (inarticulateness) and etc during their channel and collateral convalescent period of ischemia apoplexy, and its efficacy is supported by clinical trial data.

It may be useful for treating other types of stroke than cerebro-vascular stroke such as cardio-vascular disease (heart stroke mainly due to coronary artery stroke) as well as other neurological disorders. Neurological disorders are disorders that affect the central nervous system, the peripheral nervous system and the autonomic nervous system such as neurodegenerative diseases (for example, Alzheimer's disease and Parkinson's disease), epilepsy, seizure, demyelinating diseases (for example, multiple sclerosis), cerebral palsy, traumatic injuries to or tumours in the brain, spinal cord and peripheral nerves.

NeuroAid® is capable of use as a Western medicine or a dietary supplement to provide nutrition to healthy individuals as well as patients afflicted with stroke or neurological disorders.

NeuroAid® is typically administered orally (per os) as such or by diluting the capsules in water or via a gastric tube, 3 times each day and 4 capsules each time for a 4-week course of treatment. The duration of treatment is typically 3 months/3 courses, adaptable with regard to the patient's condition.

The use of TCM is, however, particularly challenging for European clinicians because of the lack of guidelines, clinical data and the small number of studies conducted under Western guidelines. Potential interactions between TCM and Western medicine that may lead to adverse side effects are also a major concern among both practitioners of TCM and Western medicine. Of particular concern are the increase or decrease in the effects of a blood thinner such as Warfarin that may lead to either a bleeding episode or formation of a blood clot, and the decrease in the effect of a blood pressure medication that may lead to high blood pressure and a stroke. For example, the potential interaction of the Chinese herb salvia with the Western drug Warfarin leading to excessive blood thinning with bleeding has been well documented with confirmatory laboratory studies. Non-steroidal anti-inflammatory drugs (NSAIDS), in particular aspirin, also have the potential to interact with Chinese herbs and increase bleeding risks. For these, and other reasons, TCM is generally not used in conjunction with Western medicines.

As current treatment options do not address the needs of difficult-to-treat patients with important stroke disabilities, such as hemiparalysis or aphasia, the present invention seeks to combine TCM with established agents for the treatment of stroke patients to present a new therapeutic treatment option for stroke patients.

SUMMARY

According to a first aspect, there is provided a composition comprising:
  (A) at least one of the following components: DanGui, Honghua, Taoren, and Deer Horn; and
  (B) at least one of the following components: Radix Astragali root (Membranous Milkvetch root or Huang Qi), Radix et Rhizoma Salviae Miltiorrhizae root (Red Sage root or Dan Shen), Radix Paeoniae Rubra root (Red Peony root or Chi Shao), rhizome of *Ligusticum Chuanxiong* (Chuan Xiong), Radix et Rhizoma Notoginseng (Sanqi), Cortex moutan (Peony or Mudanpi), Wood of Odoriferous Rosewood (Jiang Xiang), dried body of Scorpion (Quan Xie), Radix Polygalae root (Yuan Zhi), Grassleaf sweetflag rhizome (Shi Changpu), Leeches (Hirudo or Shuizhi), Ground Beetle (or Tu Bie Chong), Natural or Artificial Cow-bezoar (calculus Bovis artifactus or Rengong Niuhuang), Gambirplant stem with hooks (Ramulus uncariae cum uncis or Gou Teng).

In one embodiment, there is provided a composition as defined in the first aspect, wherein for (A), the composition comprises at least 2, 3 or 4 of DanGui, Honghua, Taoren, and Deer Horn. Optionally, for (B), the composition comprises at least 4, 5, 6, 7, 8, 9, 10, 11, 12, 13 or 14 of the components as defined in the first aspect. In yet another embodiment, the composition further comprises an agent used in Western medicine for the treatment of cerebral stroke, heart stroke, neurodegenerative diseases, brain trauma, nervous system trauma or conditions related to neuroplasticity.

Optionally, any one of (A) and (B) are present as separate formulations. Furthermore, any one of the composition as defined above and Western medicine may be present as separate formulations.

According to a second aspect, there is provided a composition as defined in the first aspect for use as a medicament.

According to a third aspect, there is provided the use of the composition as defined above, in the manufacture of a medicament for treating a patient having a condition selected from the group of cerebral stroke, heart stroke, neurodegenerative diseases, brain trauma, nervous system trauma and conditions related to neuroplasticity.

According to a fourth aspect, there is provided a product comprising:
   a composition as claimed in any one of claims 1 to 3;
   an agent used in Western medicine for the treatment of stroke, for simultaneous, separate or sequential use in the treatment of patient with a cerebral stroke, heart stroke, neurodegenerative diseases, brain trauma, nervous system trauma or conditions related to neuroplasticity; and
   optionally instructions for use of the product.

According to a fifth aspect, there is provided a kit treating a patient for a cerebral stroke, heart stroke, neurodegenerative diseases, brain trauma, nervous system trauma or conditions related to neuroplasticity, the kit comprising:
   a composition as claimed in any one of claims 1 to 3; and
   instructions for administering said composition to a patient.

The kit may further comprise an agent used in Western medicine for the treatment of stroke, for simultaneous, separate or sequential use in the treatment of the patient.

According to a sixth aspect, there is provided a method of treating a patient having a condition selected from the group of cerebral stroke, heart stroke, neurodegenerative diseases, brain trauma, nervous system trauma and conditions related to neuroplasticity, the method comprising administering to the patient a composition as define above.

The method may further comprise administering an agent used in Western medicine for the treatment of cerebral stroke, heart stroke, neurodegenerative diseases, brain trauma, nervous system trauma or conditions related to neuroplasticity.

GLOSSARY OF TERMS

This section is intended to provide guidance on the interpretation of the words and phrases set forth below (and where appropriate grammatical variants thereof).

As used herein, the term "about" as used in relation to a numerical value means, for example, ±50% or ±30% of the numerical value, preferably ±20%, more preferably ±10%, more preferably still ±5%, and most preferably ±1%. Where necessary, the word "about" may be omitted from the definition of the invention.

The term "comprising" means "including" or "consisting". Thus, for example, a composition "comprising" X may consist exclusively of X or may include one or more additional components.

The term "treatment" includes any and all uses which remedy a disease state or symptoms, prevent the establishment of disease, or otherwise prevent, hinder, retard, or reverse the progression of disease or other undesirable symptoms in any way whatsoever. Hence, "treatment" includes prophylactic and therapeutic treatment.

By "a cerebral stroke patient" we include a patient who has suffered an ischemic or haemorrhagic cerebral stroke. A cerebral stroke is a sudden and permanent death of brain cells that occurs when the flow of blood is blocked and oxygen cannot be delivered to the brain. Ischaemic stroke most commonly occurs when the flow of blood is prevented by clotting (known as 'thrombosis' of the artery) or by a detached clot that lodges in an artery (referred to as an 'embolic stroke'). Haemorrhagic stroke results from rupture of an artery wall, and from blood leaking into the surrounding brain. Haemorrhagic stroke, like ischemic stroke, causes the death of tissue by depriving the brain of blood and oxygen, and results in a number of neurological disabilities (motor, speech) as well as functional disabilities.

The term "stroke" refers to the sudden death of tissue cells due to a lack of oxygen when the blood flow is impaired by blockage or rupture of an artery. Stroke is a vascular accident that can occur in the brain or in the cardiac system. The latter condition is medically known as "myocardial infarction" and more commonly known as a "heart attack". Because of the similarity of both stroke mechanisms, it may be useful to use NeuroAid® to help patients with a heart stroke recovering better from their disability.

DETAILED DESCRIPTION

The present invention provides a new combination treatment for patients having one or more of the following conditions: cerebral stroke, heart stroke, neurodegenerative diseases, brain trauma, nervous system trauma or conditions related to neuroplasticity.

The present invention provides methods and compositions for treating patients having a condition selected from the group consisting of cerebral stroke, heart stroke, neurodegenerative diseases, brain trauma, nervous system trauma and conditions related to neuroplasticity. The patients are administered with:
   (A) at least one of DanGui, Honghua, Taoren, and Deer Horn; and
   (B) at least one of a composition which comprises at least 1, 2, 3, 4, 5, 6, 7, 8, 9, 10, 11, 12, 13 or 14 of the following ingredients: Radix Astragali root (Membranous Milkvetch root or Huang Qi), Radix et Rhizoma Salviae Miltiorrhizae root (Red Sage root or Dan Shen), Radix Paeoniae Rubra root (Red Peony root or Chi Shao), rhizome of *Ligusticum Chuanxiong* (Chuan Xiong), Radix et Rhizoma Notoginseng (Sanqi), Cortex moutan (Peony or Mudanpi), Wood of Odoriferous Rosewood (Jiang Xiang), dried body of Scorpion (Quan Xie), Radix Polygalae root (Yuan Zhi), Grassleaf sweetflag rhizome (Shi Changpu), Leeches (Hirudo or Shuizhi), Ground Beetle (or Tu Bie Chong), Natural or Artificial Cow-bezoar (calculus Bovis artifactus or Rengong Niuhuang), Gambirplant stem with hooks (Ramulus uncariae cum uncis or Gou Teng); and
   (i) an agent used in Western medicine for the treatment of stroke.

This invention is based on the discovery that NeuroAid® is not only efficacious in treating stroke patients but that it may be safely used in combination with treatments commonly used in Western medicine for treating stroke patients without adverse side effects such as haemostasis disorders or high blood pressure as described above.

As chronic forms of neurodegeneration such as Alzheimer's and Parkinson's disease (associated with cognitive dysfunction) share common mechanisms of neuronal death with acute forms of neurodegeneration which accompanies stroke, head trauma, cardiac arrest and subarachnoid hemorrhage, NeuroAid® may be useful to improve or treat these brain disorders as it is believed to have potential activity on neuroprotection or on plasticity. Neuroplasticity (also referred to as brain plasticity or cortical plasticity) refers to changes that occur in the organization of the brain and its circuits of neurons, in particular changes that occur to the location of specific information processing functions. This process supports the learning of new functions as the result of experience during development as mature animals and the creation of new information with healthy neurons by-passing damaged neurons affected by trauma or a medical condition.

Hence, in addition to treating cerebral stroke patients it is envisaged that NeuroAid® or a NeuroAid®-like composition (e.g. a composition according to (i) above), optionally in combination with available agents used in Western medicine, may be useful for the treatment of such neurodegenerative diseases. Typically, the Western medicine used in combination with NeuroAid® or a NeuroAid®-like composition is one that targets a different mechanism from NeuroAid® or a NeuroAid®-like composition. For example, the Western medicine may be antiplatelets and anticoagulants typically used in secondary stroke prevention, and neuroprotectants typically used in improving recovery potential in the acute phase of stroke via mechanisms described below.

NeuroAid® and Similar Compositions

The ingredients set forth in (i) above may be present in the composition in a relatively crude form (e.g. unprocessed or crushed herbs) or in a more refined form (e.g. purified extracts).

In one embodiment, NeuroAid® is used. NeuroAid® is a TCM product in capsule form comprising 9 herbal components and 5 animal components. NeuroAid® comprises Radix Astragali root (Membranous Milkvetch root or Huang Qi), Radix et Rhizoma Salviae Miltiorrhizae root (Red Sage root or Dan Shen), Radix Paeoniae Rubra root (Red Peony root or Chi Shao), rhizome of *Liguisticum Chuanxiong* (Chuan Xiong), Radix et Rhizoma Notoginseng (Sanqi), Cortex moutan (Peony or Mudanpi), Wood of Odoriferous Rosewood (Jiang Xiang), dried body of Scorpion (Quan Xie), Radix Polygalae root (Yuan Zhi), Grassleaf sweetflag rhizome (Shi Changpu), Leeches (Hirudo or Shuizhi), Ground Beetle (or Tu Bie Chong), Natural or Artificial Cow-bezoar (calculus Bovis artifactus or Rengong Niuhuang), Gambirplant stem with hooks (Ramulus uncariae cum uncis or Gou Teng). NeuroAid® may further comprise any one or more of DanGui, Honghua, Taoren, or Deer Horn NeuroAid®, which may be registered under different names in different countries (e.g. in South Africa it is marketed as Strocaid® or Danqi Piantan Jiaonang®) is manufactured by and available commercially in the People's Republic of China from Tianjin Shitian Pharmaceutical Group Co., Ltd (located in the Jianxin Industrial area, Wangwenzhuang town, Xiqing district, Tianjin City, China; Postal Code 300381;). It is also available from Moleac Pte Ltd (formerly Molecular Acupuncture Pte Ltd), the main licensee outside of the People's Republic of China (11 Biopolis Way, Helios #09-08 Singapore ; Tel: 65 64789430; Fax: 6564789435).

For the avoidance of doubt, NeuroAid® not only includes NeuroAid® in the form in which it is currently marketed but also includes future formulations of NeuroAid® which may, for example, be marketed by Tianjin Shitian Pharmaceutical Group Co., Ltd or Moleac Pte Ltd. Such future formulations may, for example, vary in dosage amounts or the concentration of its active ingredients etc.

Combination Therapy with NeuroAid®

In the present invention, NeuroAid® can be used in combination with one or more agents used in Western medicine for the treatment of stroke. By "an agent used in Western medicine", we include any form of mainstream medicine or Western medicine, including dietary supplements. For the avoidance of doubt, by "an agent used in Western medicine", we do not include medicaments used in TCM medicaments or the like.

Examples of suitable agents include antiplatelets, anticoagulants, neuroprotectants, compounds for treating stroke and compounds for activating potassium channels TREK-1. One, two, three, four, five or more of such further agents may, for instance, be used in combination with NeuroAid®. Thus, the following are envisaged as suitable examples for use as combination partner (ii): an antiplatelet; an anticoagulant; a neuroprotectant; a compound for treating stroke; a compound for activating potassium channels TREK-1; an antiplatelet in combination with an anticoagulant; an antiplatelet in combination with a neuroprotectant; an antiplatelet in combination with a compound for treating stroke; an antiplatelet in combination with a compound for activating potassium channels TREK-1; an anticoagulant in combination with a neuroprotectant; an anticoagulant in combination with a compound for treating stroke; an anticoagulant in combination with a compound for activating potassium channels TREK-1; a neuroprotectant in combination with a compound for treating stroke; a neuroprotectant in combination with a compound for activating potassium channels TREK-1; a compound for treating stroke in combination with a compound for activating potassium channels TREK-1; an antiplatelet in combination with an anticoagulant and a neuroprotectant; an antiplatelet in combination with an anticoagulant and a compound for treating stroke; an antiplatelet in combination with an anticoagulant and a compound for activating potassium channels TREK-1; an antiplatelet in combination with a neuroprotectant and a compound for treating stroke; an antiplatelet in combination with a neuroprotectant and a compound for activating potassium channels TREK-1; an antiplatelet in combination with a compound for treating stroke and a compound for activating potassium channels TREK-1; an anticoagulant in combination with a neuroprotectant and a compound for treating stroke; an anticoagulant in combination with a neuroprotectant and a compound for activating potassium channels TREK-1; an anticoagulant in combination with a compound for treating stroke and a compound for activating potassium channels TREK-1; a neuroprotectant in combination with a compound for treating stroke and a compound for activating potassium channels TREK-1; an antiplatelet in combination with an anticoagulant, a neuroprotectant and a compound for treating stroke; an antiplatelet in combination with an anticoagulant, a neuroprotectant and a compound for activating potassium channels TREK-1; an antiplatelet in combination with an anticoagulant, a compound for treating stroke and a compound for activating potassium channels TREK-1; an antiplatelet in combination with a neuroprotectant, a compound for treating stroke and a compound for activating potassium channels TREK-1; an anticoagulant in combination with a neuroprotectant, a compound for treating stroke and a compound for activating potassium channels TREK-1; and an antiplatelet in combination with an anticoagulant, a neuroprotectant, a compound for treating stroke and a compound for activating potassium channels TREK-1.

Antiplatelet Agents

Antiplatelet agents are medications that block the formation of blood clots by preventing the clumping of platelets. Examples of antiplatelet agents include without limitations:

Aspirin, the thienopyridine derivatives such as ticlopodine (Ticlid) and clopidogrel (Plavix), the Phosphodiesterase III inhibitors such as Cilostazol (Pletal), Adenosine re-uptake inhibitors such as Dipyridamole (Persantine or Aggrenox (in combination with aspirin)), and the glycoprotein IIb/IIIa inhibitors such as Abciximab (ReoPro), Eptifibatide (Integrilin) and Tirofiban (Aggrastat) and orally active RGD mimetic prodrugs such as Orbofiban, Sibrafiban, SR121566, or Roxifiban.

These agents differ in the way in which they prevent platelets from clumping: for example, Aspirin (Cyclo-oxygenase inhibitor) blocks thromboxan A-2 by inhibiting the enzyme cyclo-oxygenase-1 (COX-1), the thienopyridine derivatives (ADP inhibitors) block the adenosine diphosphate (ADP) receptor on the surface of platelets membrane, and glycoprotein IIB/IIa inhibitors prevent platelet aggregation by inhibiting a different receptor at the surface of platelets (the attachment of glycoprotein IIb/IIIa to its receptor is the final step in all pathways that cause platelets aggregation).

One or more antiplatelet agents can be employed in the present invention, for instance, a combination of, for example, 2 or 3 or more antiplatelet agents may be employed.

Anticoagulant Therapies

Antiplatelet agents are part of anticoagulation therapies. There are two other groups of anticoagulant agents which may also be employed in the present invention:

Inhibitors of clotting factor synthesis such as without limitation, vitamin K antagonists like coumarins or indanedione derivatives (Warfarin or Coumadin).

Inhibitors of thrombin that include several products such as, but not limited to Heparin (Standard Unfractionated Heparin (UFH), Low Molecular Weight Heparin (LMWH) such as Enoxaparin, Tinzaparin) or to recombinant forms of hirudin such as desirudin and lepirudin (Refludan).

Neuroprotectants

Using various mechanisms, neuroprotectants are compounds that preserve neuronal tissue at risk of dying during stroke and in the aftermath of stroke. Some neuroprotectant agents are sometimes used to treat human stroke patients and include antioxidants (e.g. selenium, 30 vitamin E, vitamin C, glutathione, cysteine, flavinoids, quinolines, enzymes with; reducing activity, etc), N-methyl-D-aspartate Receptor Antagonists (Dextrorphan, Selfotel, Magnesium), Narcotic Receptor antagonist (Nalmefene (Cervene), Ca-channel blockers, Na-channel modulators (Lubeluzole), Alpha-aminobutyric acid agonist (Clomethiazole), glutamate receptor modulators, serotonin receptor agonists (repinotan), phospholipids, free-radical scavenger (Tirilazad, and NXY-059), astrocyte activation inhibitor (ONO 2506), monoclonal antibodies such as anti-ICAM-1 (Enlimomab), Human anti-leukocytic antibody, Hu23F2G, membrane stabilization agent CDP-choline (Citicholine), Fibroblast growth factor (Fiblast), unsaturated- and polyunsaturated fatty acids, estrogens and selective estrogen receptor modulators (SEAMS), progestins, thyroid hormone and thyroid hormone-mimicking compounds, cyclosporin A and derivatives, thalidomide and derivatives, methylxanthines, Mono-Amine-Oxydase inhibitors (IMAO), serotonin-, noradrenaline and dopamine uptake blockers, dopamine I agonists, L-DOPA, nicotine and derivatives, and NO synthase modulators.

Compounds for Treating Stroke

Compounds used to treat human stroke patients include Calcium Channel Blockers (D-600, Diltiazem, Nitrendipine, Nimodipine, Nifedipine, Flunarizine, Fluspirilene, Isradipine, Nicardipine, PY 108-068, Verapamil and Triapamil), Calcium chelator (DP-b99), free radical scavengers (Ebselen, Tirilazad, NXY-059), GABA receptor agonists (Diazepam, Baclofen), AMPA agonists (ZK 200775/MPQX), competitive NMDA antagonists (aptiganel/cerestat, CP 101,606, dextrophan, MK 801/dizocilpine, remacemide), glycine site antagonists (GV 150526, ACEA 1021), polyamine site antagonists (eliprodil), growth factors (bFGF), Sodium channel blockers (fosphenytoin, 619C89), potassium channel opener (BMS 204352, cromakalim, levcromakalim, aprikalim, pinacidil, diazoxide, nicorandil, minoxidil), piracetam, adenosine transport inhibitor (propentofylline), gangliosides GM (non NMDA antagonist), presynaptic glutamate release inhibitors, clazosentan, desmoteplase, viprinex (ancrod), tenecteplase (TNKase; Metalyse), alteplase, cyclic nitrones, TWEAK (TNF-like weak inducer of apoptosis) receptor, thrombolytica treatments (urokinase, streptokinase, t-PA/tissue plasminogen activator or recombinant urokinase), anistreplase, riluzole, and disufenton sodium (NXY 059), candesartan, AX-200 (G-CSF, Fligrastim), caffeinol (caffeine+ethanol), enecadin, microplasmin, sonolysis+tPA, V-10153, HTUPA, solulin, piclozotan, S-0139, S-18986, AEOL-10150, AL-208, KN-38-7271, phridoxal 5-phosphate, Neu-2000KL, ONO-2231, PGX-100, RVX-208, SUN-N4057, SUN-N8075, TAT-NR2B9c, GLP-1-expressing stem cell therapy, Msc-1 (SA-4503, AGY-94806)), NH-02D, S-0139 259, tissue protective cytokines (Lu-AA24493), V10153 270 (BB-10153, TAPgen), combined use of statins and other cholesterol lowering drugs, erythropoietin, cerebrolysin and CDP-choline (cytidine-5'-diphosphocholine).

Compounds for Activating Potassium Channels TREK-1

Other suitable agents used in Western medicine include compounds capable of activating the potassium channels TREK-1. The activation of TREK-1 has been found to have a neuroprotective effect. In addition, TREK-1 has been shown to play a major role in neuroprotection against epilepsy and brain and spinal chord ischemia. Since NeuroAid® does not activate potassium channels TREK 1, compounds that are capable of activating the potassium channels TREK-1 may be used in combination with NeuroAid® to enhance the neuroprotective effect of NeuroAid®.

One example of a compound that is capable of activating the potassium channels TREK-1 is Polyunsaturated fatty acids (PUFAs). Polyunsaturated fatty acids are fatty acids that contain more than one double bond. PUFAs can be categorized as methylene-Interrupted Polyenes or Conjugated fatty acids.

Methylene-Interrupted Polyenes are fatty acids that have two or more cis double bonds that are separated from each other by a single methylene group. The essential fatty acids are all omega-3 and -6 methylene-interrupted fatty acids. Examples of Omega-3 fatty acids include without limitation: Alpha-linolenic acid (ALA), Stearidonic acid (STD), Eicosatrienoic acid (ETE), Eicosatetraenoic acid (ETA), Eicosapentaenoic acid (EPA), Docosapentaenoic acid (DPA), Docosahexaenoic acid (DHA), Clupanodonic acid, Tetracosapentaenoic acid, Tetracosahexaenoic acid or Nisinic acid. Examples of Omega-6 fatty acids include without limitation: Linoleic acid (LIN), Gamma-linolenic acid (GLA), Eicosadienoic acid, Dihomo-gamma-linolenic acid (DGLA), Arachidonic acid (AA), Docosadienoic acid, Adrenic acid, Docosapentaenoic acid or Osbond acid. Omega-9 fatty acids are also methylene-Interrupted polyenes, and may be monosaturated or polysaturated. Examples of Omega-9 fatty acids include without limitation: Oleic acid, Eicosenoic acid, Mead acid, Erucic acid or Nervonic acid.

Conjugated fatty acids are fatty acids that have two or more conjugated double bonds. Examples of Conjugated fatty acids include without limitation: Remenic acid, α-Calendic acid, β-Calendic acid, Jacaric acid, α-Eleostearic acid, β-Eleostearic acid, Catalpic acid, Punicic acid, Rumelenic acid, α-Parinaric acid, β-Parinaric acid, Bosseopentaenoic acid.

Some other PUFAs which are not catergorized as methylene-Interrupted Polyenes or Conjugated fatty include without limitation: Pinolenic acid and podocarpic acid.

Other compounds that may be capable of activating the potassium channels TREK-1 include the drug Riluzole (Rilutek®), Lysophospholids (LPLs), Caffeic Acid esters and Xenon. These compounds may also be used in combination with NeuroAid® to enhance the neuroprotective effect of NeuroAid®.

Modes of Administration

The combination partners (i) and (ii) may be present in a single formulation or may be present as separate formulations. In one embodiment there may be a synergistic effect. As mentioned above, combination partner (ii) may comprise more than one agent, for example, two antiplatelet agents, or an antiplatelet agent and a neuroprotectant may be used.

The combination partners (i) and (ii) may be administered to the patient at the same time (e.g. simultaneously) or at different times (e.g. sequentially) and over different periods of time, which may be separate from one another or overlapping. The combination partners (i) and (ii) may be administered in any order.

The combination partner (ii) utilized and the appropriate administration route and dose level will be known to those in the art or could be readily determined by one skilled in the art. Typically, as is well known in the medical art, dosage regimens may depend on various factors including the patient's size, body surface area, age, the particular compound to be administered, sex, time and route of administration, general health, and other drugs being administered concurrently. While individual needs vary, determination of optimal ranges of effective amounts of each component is within the skill of the art. The dosage would be similar to that administered when the agent is used without NeuroAid®.

Dosage amounts for ticlopidine and for dipyridamole are described in the Physicians' Desk Reference, as are dosage amounts for other antiplatelet and neuroprotectant agents. Dosage amounts of aspirin for the indicated effects are known to those skilled in the medical arts, and generally range from about 20 mg to about 325 mg per day. For example, a formulation may contain about 20 mg, 30 mg, 80 mg, 160 mg, 250 mg, 300 mg, 325 mg or 350 mg of aspirin.

NeuroAid® may be administered orally as such, typically with four 0.4 g capsules being taken 3 times a day. For patients with swallowing difficulties, capsules may be opened and powder diluted in water that can be drunk as such or injected via a gastric tube. Hence, a daily dose of about 4.8 g is envisaged. In one embodiment, the patient's daily dose of NeuroAid® (or other composition according to (i) above) is about 2 g to 8 g; 3 g to 7 g; 4 g to 6 g; 4.25 g to 5.75 g; 4.5 g to 5.25 g; 4.5 g to 5 g; 4.6 g to 4.10 g; or 4.7 g to 4.9 g. A "daily dose" can be a single tablet or capsule etc. or multiple tablets or capsules etc. to be taken on a given day. Suitably, the composition according to (i) is taken orally.

In one embodiment, each course of NeuroAid® treatment lasts about 4 weeks. Typically 3 courses are administered, most commonly back to back. No therapeutic window is required but additional courses can be added even after a few days of treatment cessation. Hence, in one embodiment, each NeuroAid® treatment lasts about 12 weeks. In another embodiment, the treatment course of NeuroAid® (or other composition according to (i) above) is about 4 to 24 weeks; 7 to 16 weeks; 9 to 15 weeks; 10 to 14 weeks; or 11 to 13 weeks.

In instances of ischemic stroke, treatment with anti-platelet drugs usually commences as soon as possible after onset of stroke symptoms while in instances of haemorrhagic stroke, anticoagulation treatments such as Coumadin or Heparin, are highly contra-indicated and discontinued immediately if they were part of patient's usual treatment. Protamine and vitamin K may be given to reduce bleeding in patients with anticoagulant-induced bleeding.

In addition to combination partners (i) and (ii), other compounds may be administered, for example, proton pump inhibitors such as Nexium, Protonix and Aciphex. Daily doses of proton pump inhibitors are typically administered to reduce the risk of ulcer development and bleeding in patients under long-term low-dose aspirin or antiplatelet therapy.

BRIEF DESCRIPTION OF DRAWINGS

FIG. 1 Phase II clinical trial results on use of NeuroAid® versus BNJ (a) Neurological deficit improvement (DTER scores) before and after treatment with NeuroAid® or BNJ (b) Functional outcomes before and after treatment with NeuroAid® or BNJ.

FIG. 2 Phase III clinical trial results on use of NeuroAid® versus BNJ (a) Neurological deficit improvement (DTER scores) before and after treatment with NeuroAid® or BNJ (b) Functional outcomes before and after treatment with NeuroAid® or BNJ.

FIG. 3 Clinical study results on the interaction between NeuroAid® and aspirin in healthy volunteers and its effect on blood pressure. (a) systolic blood pressure (b) diastolic blood pressure.

For FIGS. 1 and 2:

Level of severity of stroke (DTER scores)=LOW, MILD, COMMON, SEVERE Functional outcomes: 0 pts=able to take care of oneself and speak freely; 2 pts=able to live independently and to do some simple work with some incomplete functions; 4 pts=able to walk and take care of oneself but must be helped partially; 6 pts=able to stand and take a step but must be taken care of at all times; 8 pts=confined to bed.

EXAMPLES

In the following examples, tables and drawings, the term "NeuroAid®" refers to a composition that is the same as NeuroAid®.

Example 1

Phase II Trial: NeuroAid® Versus Buchang Naoxintong Jioanang (BNJ)

A randomized, double-blinded, stratified, control design was adopted for the clinical trial on the efficacy of NeuroAid® in treating patients suffering from apoplexy compared to BNJ which is known for its effectiveness in treating patients suffering from apoplexy (see Example 3). A total of 200 subjects were involved; 100 cases were treated with NeuroAid® while 100 cases were treated with BNJ (control). BNJ is produced and provided by Xianyang Buchang Pharmaceutical Co., Ltd. Four capsules of each drug were administered 3 times daily, with each course of treatment lasting 4 weeks.

The evaluation criteria for neurological and functional recovery from apoplexy (DTER scoring diagnostic standard) and TCM symptom therapeutic effects (TCM diagnostic symptom scoring standard) were assessed in accordance with the Clinical Guiding Principles for the Treatment of Apoplexy with New Chinese Herbs promulgated by the Ministry of Health of the PRC in 1993. Severity of symptoms in the DTER scoring standard was classified according to 4 levels (SEVERE, COMMON, MILD and LOW) while functional outcomes were classified in points from 0 to 8.

Figure 1A:
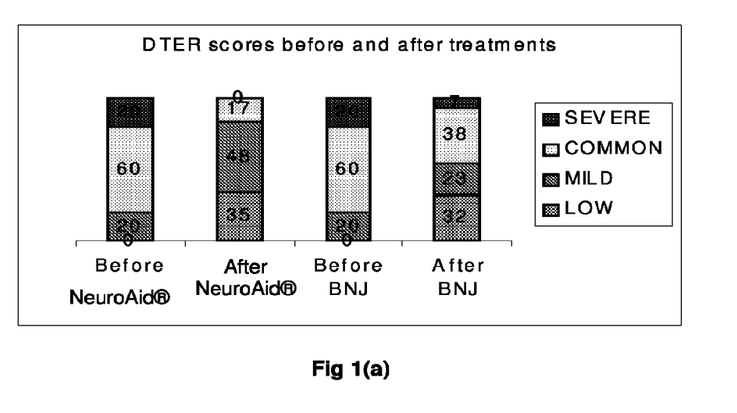
Figure 1B:
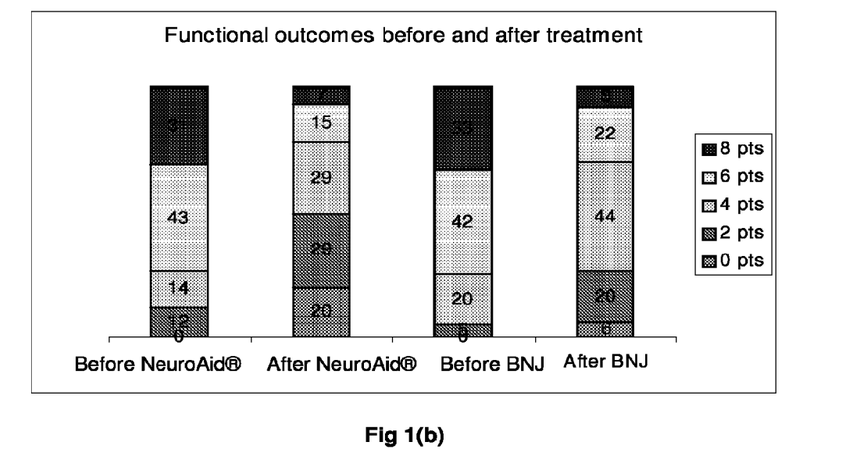

The data (FIG. 1) demonstrated NeuroAid®'s clinical efficacy and superiority in improving patients' neurological deficit and functional (autonomy/dependency post-stroke) outcomes versus that of the control treatment BNJ.

Example 2

Phase III Trial: NeuroAid® Versus BNJ

A randomized, double-blinded, stratified, control design was adopted. A total of 405 subjects were involved, where 300 cases were treated NeuroAid® while 105 cases were treated with the control drug BNJ produced and provided by Xianyang Buchang Pharmaceutical Co., Ltd. Four capsules of each drug were administered 3 times daily, with each course of treatment lasting 4 weeks.

The evaluation criteria for neurological and functional recovery from apoplexy (DTER scoring diagnostic standard) and TCM symptom therapeutic effects (TCM diagnostic symptom scoring standard) were assessed as in the Phase II trial.

Figure 2A:
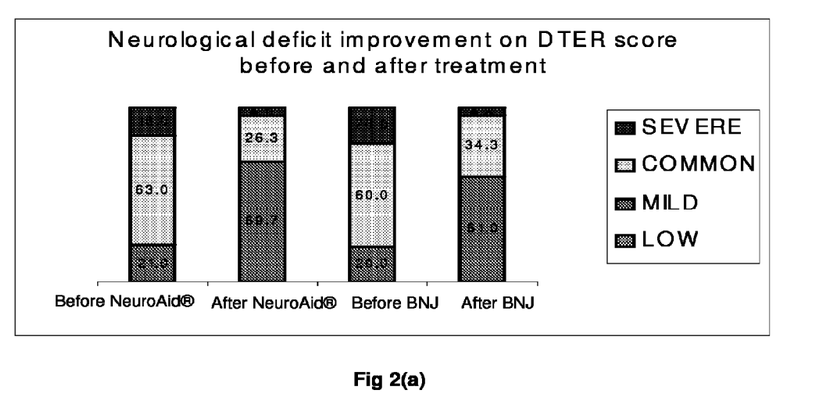
Figure 2B:
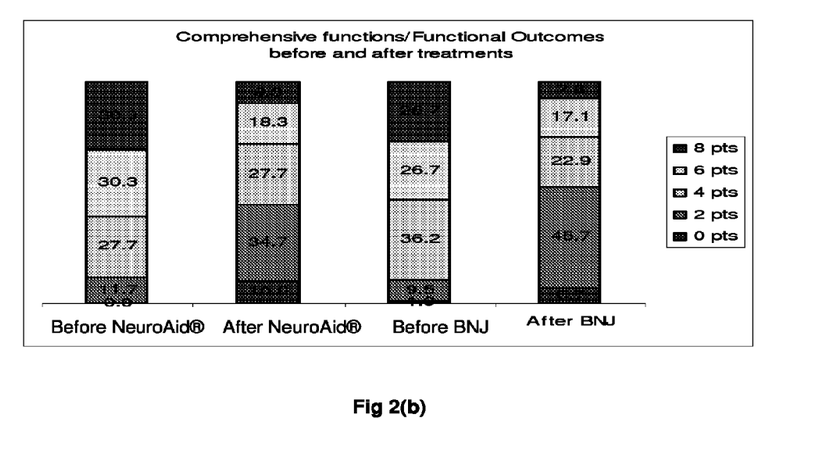

The data (FIG. 2) demonstrated that NeuroAid® was superior to BNJ in improving the patients' neurological deficit particularly in helping patients recover from their hemi-paralysis. With regard to functional outcomes, even if NeuroAid® failed to demonstrate any superiority to BNJ, both treatments had comparable effect and about 50% of the stroke patients included in the study returned to a functionality dependent state after 4 weeks of treatment (comprehensive function score similar to Rankin score used in the West equal to 0 or 2).

No adverse effects of treatment with NeuroAid® were observed in the Phase II or Phase III trials. The finding of a broad therapeutic window (>14 days after stroke onset) in both trials also gives a huge advantage over fibrinolytic agents, which have to be given within the first 3 to 6 hours.

Example 3

Comparative Study on Efficacy of BNJ Versus Citicoline and Aspirin

A randomized, double-blinded, stratified, control design was adopted for the comparative study on the efficacy of BNJ and Citicoline in treating patients with apoplexy. Citicoline is the only putative neuro-protectant that has shown results in Western randomized, double-blinded trials given within 24 hours after symptom onset. Davalos et al. (Oral Citicoline in Acute Ischemic Stroke. An Individual Patient Data Pooling Analysis of Clinical Trials (2002) *Stroke* 33:2850) documents the ability of Citicoline to improve complete recovery at 3 months.

A first comparative study performed in the PRC involved 150 subjects treated with Citicoline (0.5 g IV) for 15 days in combination with a TCM (Xueshuantong) and 160 subjects treated with Citicoline (0.5 g IV) for 15 days in combination with Xueshuantong and BNJ. The latter group treated with BNJ showed improvements in scores on a neuro-functional defects scale, plasma viscosity level and cholesterol level.

A second comparative study compared 30 subjects treated with aspirin (150 mg), Citicoline (0.75 g IV) and salvia miltiorrhizae injection (60 mL), with 30 subjects treated with aspirin (150 mg), Citicoline (0.75 g IV), salvia miltiorrhizae injection (60 mL) and BNJ for 1 month. The BNJ-treated group showed significantly better results in neurological and functional outcomes.

Citicoline (CDP-choline) is a key intermediary in the biosynthesis of phosphatidylcholine, an important component of the neural cell membrane that stabilizes cells membranes and inhibits the formation of cytotoxic free fatty acids. It has been shown to produce beneficial effects in both animal models and clinical stroke trials. A significant difference between the groups, favoring citicoline treatment, was seen in terms of functional outcome as measured by the Barthel Index and Rankin scale, neurologic evaluation as measured by the National Institutes of Health (NIH) stroke scale, and cognitive function as measured by the Mini Mental Status Examination. [1] As efficacy trials on Citicoline have been demonstrated to be superior to the placebo, it can be inferred from the above two comparative studies that treatment with BNJ would likewise be superior to a placebo.

Example 4

Safety Study: Phase IV Open-Label Study on Effect of NeuroAid® on Hemostasis

Blood samples of 30 healthy individuals were collected before they received NeuroAid® and 2 and 8 hours after NeuroAid® initiation (4 capsules). Five coagulation tests were performed on the blood samples.

TABLE 1

| Blood Sampling | First (%) | Second (%) | Third (%) |
|---|---|---|---|
| Quick Prothrombine Time | | | |
| Average | 12.75 | 12.71 | 12.92 |
| Std Deviation | 0.68 | 0.72 | 0.67 |
| Activated Partial Prothrombine Time | | | |
| Average | 37.64 | 37.15 | 38.66 |
| Std Deviation | 4.28 | 4.44 | 4.26 |
| Fibrinogen | | | |
| Average | 2.98 | 3.05 | 3.06 |
| Std Deviation | 0.61 | 0.59 | 0.57 |
| Platelet Aggregation | | | |
| Average | 63.01 | 62.19 | 61.52 |
| Std Deviation | 15.50 | 12.08 | 13.37 |
| D-Dimer | | | |
| Control Device | 2.7 | 2.4 | 1.9 |

The results confirmed that NeuroAid® has no effect on hemostasis blood factors and thus does not increase bleeding risks.

Example 5

Safety Study: Phase IV Open-Label Study on Potential Interaction Between NeuroAid® and Acetylsalicylic Acid (Aspirin) in Healthy Volunteers and its Effect on Hemostasis and Blood Pressure An open randomized one-day study was conducted on 11 healthy volunteers receiving NeuroAid® treatment (12 capsules per day) and aspirin (ASA 300 mg per day) from day 1 to day 5, and 11 healthy volunteers receiving aspirin alone (300 mg per day) from day 1 to day 5. Blood samples of the subjects were collected before they received treatment and 2 and 8 hours after treatment initiation. The blood samples were analyzed with the 5 coagulation tests, namely quick prothrombine time, activated partial prothrombine time, fibrinogen dosage, platelet aggregation and D-dimer, to identify the coagulation mechanisms triggered by potential interaction between NeuroAid® and aspirin. Blood pressure of the 22 subjects was also measured before treatment, and 2, 4, 6 and 8 hours after treatment initiation.

Figure 3A:
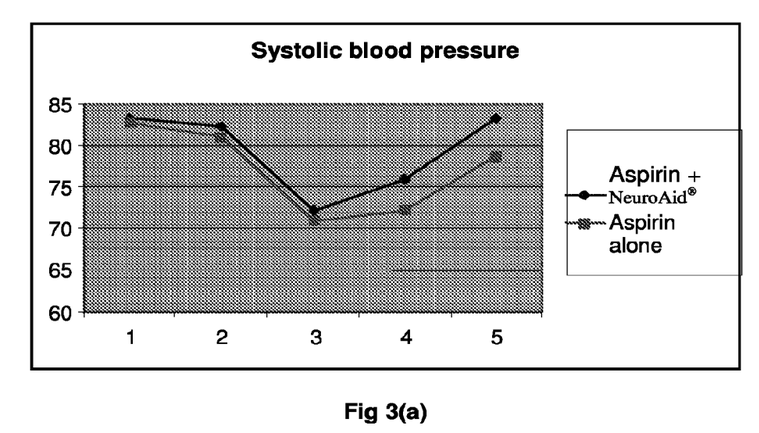
Figure 3B:
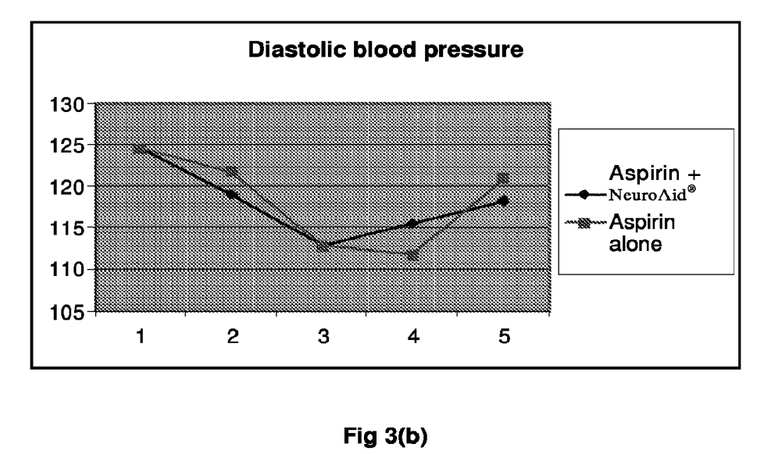

Results of this trial show that NeuroAid® can be safely associated with aspirin and does not have any interaction with aspirin regarding blood coagulation (Table 2) and blood pressure (FIG. 3).

TABLE 2

|  | Mean |
|---|---|
| Quick Prothrombine Time (Seconds) | |
| Aspirin alone | |
| T = 0 | 12.9 |
| T + 2 hours | 12.6 |
| T + 8 hours | 12.4 |
| Aspirin + NeuroAid ® | |
| T = 0 | 12.7 |
| T + 2 hours | 12.6 |
| T + 8 hours | 12.4 |
| Activated Partial Prothrombine Time (Seconds) | |
| Aspirin alone | |
| T = 0 | 38.8 |
| T + 2 hours | 39.0 |
| T + 8 hours | 38.2 |
| Aspirin + NeuroAid ® | |
| T = 0 | 37.1 |
| T + 2 hours | 38.2 |
| T + 8 hours | 37.2 |
| Fibrinogen (G/L) | |
| Aspirin alone | |
| T = 0 | 3.2 |
| T + 2 hours | 3.2 |
| T + 8 hours | 3.0 |
| Aspirin + NeuroAid ® | |
| T = 0 | 3.2 |
| T + 2 hours | 3.0 |
| T + 8 hours | 2.9 |
| Platelet Aggregation (Percentage) | |
| Aspirin alone | |
| T = 0 | 62.82 |
| T + 2 hours | 62.87 |
| T + 8 hours | 48.01 |
| Aspirin + NeuroAid ® | |
| T = 0 | 61.82 |
| T + 2 hours | 58.28 |
| T + 8 hours | 46.98 |
| D-Dimer (µG/L) | |
| Aspirin alone | |
| T = 0 | 0.16 |
| T + 2 hours | 0.16 |
| T + 8 hours | 0.16 |
| Aspirin + NeuroAid ® | |
| T = 0 | 0.13 |
| T + 2 hours | 0.09 |
| T + 8 hours | 0.15 |

Example 6

Safety Study: Pilot Open-label Study on Potential Interaction Between NeuroAid® and Western Drugs in Ischemic Stroke Patients and its Effect on Hemostasis and Blood Pressure A pilot open-label study was conducted on 10 ischemic stroke patients within the first week of the onset of stroke (early phase). The test patients were selected based on the following criteria:
 a) aged above 18 years old;
 b) have had a cerebral infarction with compatible imaging on Computed Tomography (CT) scan or Magnetic Resonance Imaging (MRI); and
 c) the time window between stroke onset and the open-label study was less than one week, Conversely, patients that were excluded from the study include:
 a) female patients who were pregnant, lactating or nursing;
 b) patients showing signs of intra-cerebral hemorrhage on brain Computed Tomography (CT) scan or Magnetic Resonance Imaging (MRI);
 c) patients having a history of easy bruising or blood coagulation disorders;
 d) patients receiving other Traditional Chinese Medicine than NeuroAid®;
 e) patients who received thrombolysis;
 f) patients who have used NeuroAid® within a 3-month period prior to screening and enrolment in the open-label study.

Each patient received 4 capsules of NeuroAid® 3 times a day for one month in addition to the other Western medicine the patient was receiving. The Western medicine includes platelet aggregation inhibitors, nitrates, oral anti-hypertensive drugs, lipid regulating drugs, oral anti-diabetic, or anti-convulsant drugs.

Safety assessment tests were performed on blood samples collected from the test patients at three intervals: a) before NeuroAid® intake (to form the baseline); b) 1 week after NeuroAid® initiation; and c) 4 weeks after NeuroAid® initiation. The blood samples were analyzed using the following hematology and biochemical laboratory analytical tests:
 a) Prothrombine Time (PT);
 b) Activated Partial Prothrombine Time (APPT);
 c) fibrinogene dosage;
 d) platelet aggregation;
 e) D-dimer test;
 f) blood cell count;
 g) creatinine;
 h) SGOT SGPT;
 i) glycemia; and
 j) CRP-C-reactive protein.

The results of the open-label study (Table 3) demonstrated that NeuroAid® does not have any effect on renal and hepatic functions, glycemia, and C-Reactive-protein when used in combination with Western medicine for managing risk factors of secondary stroke. For example, in the five coagulation tests (Prothrombine Time (PT), Activated Partial Prothrombine Time (APPT), fibrinogene dosage, platelet aggregation, D-dimer test) performed on Patients 4 and 5 (both receiving NeuroAid® and four different types of Western medicine) (Table 3, columns 5 and 6), the test readings taken 1 week and 4 weeks after NeuroAid® initiation do not differ significantly from the baseline readings taken before the start of NeuroAid® intake.

The statistical analysis of the readings for the open-label study (Table 4) also show that the readings from all 10 patients do not differ significantly from the mean values. For example, in the Prothrombine Time (PT) test, the Standard Deviation (SD) values after 1 week and 4 weeks of NeuroAid® initiation are 1.09 and 0.77, respectively, which do not deviate significantly from the baseline value of 0.88. Similarly, in the fibrinogen dosage test, the Standard Deviation (SD) values after 1 week and 4 weeks of NeuroAid® initiation are 1.22 and 1.11, respectively, which do not deviate significantly from the baseline value of 1.13.

Hence, the results of the open-label study further demonstrated that NeuroAid® can be safely used in combination with Western medicine such as platelet aggregation inhibitors, nitrates, oral anti-hypertensive drugs, lipid regulating drugs, oral anti-diabetic, or anti-convulsant drugs.

TABLE 3

|  | PATIENT 1 | PATIENT 2 | PATIENT 3 | PATIENT 4 | PATIENT 5 |
|---|---|---|---|---|---|
| Gender | F | F | F | M | F |
| Age | 79 | 69 | 61 | 58 | 53 |
| Day(s) from stroke onset | 3 | 4 | 1 | 2 | 7 |
| On Aspirin? | N | Y | N | Y | N |
| Other Treatment administered | NeuroAid ®, ISMN, nimodipine | NeuroAid ®, aspirin, nimodipine, gemfibrozil | NeuroAid ®, ISMN, mefformin, glipizide | NeuroAid ®, aspirin, nimodipine, glicazide, indapamide | NeuroAid ®, ISMN, nimodipine, amlodipine, KCl |
| NHSS | | | | | |
| Baseline | 19 | 1 | 16 | 7 | 6 |
| 1 Week | 17 | 0 | 8 | 4 | 4 |
| 1 Month | 15 | 1 | 7 | 4 | 3 |
| Rankin score | | | | | |
| Baseline | 5 | 1 | 5 | 4 | 3 |
| 1 Week | 5 | 1 | 4 | 2 | 1 |
| 1 Month | 5 | 1 | 4 | 1 | 1 |
| PT (secs) | | | | | |
| Baseline | 14.3 | 13.0 | 11.6 | 12.8 | 13.8 |
| 1 Week | 12.7 | 11.6 | 11.1 | 12.4 | 14.4 |
| 1 Month | 13.7 | 12.0 | 11.5 | 11.8 | 13.6 |
| APTT (secs) | | | | | |
| Baseline | 27.1 | 32.1 | 29.0 | 33.5 | 33.1 |
| 1 Week | 31.8 | 29.5 | 28.6 | 31.5 | 38.2 |
| 1 Month | 29.6 | 29.9 | 30.5 | 32.2 | 28.5 |
| Fibrinogen dosage (g/L) | | | | | |
| Baseline | 5.25 | 4.12 | 5.34 | 3.01 | 5.77 |
| 1 Week | 6.76 | 3.03 | 3.38 | 3.80 | 4.64 |
| 1 Month | 3.36 | 4.24 | 3.75 | 6.71 | 4.75 |
| Platelet agregation | | | | | |
| Baseline | 61.62 | 51.20 | 77.21 | 74.40 | 60.47 |
| 1 Week | 47.80 | 68.83 | 70.22 | 38.98 | 56.41 |
| 1 Month | 60.82 | 71.92 | 33.11 | 37.30 | 42.59 |
| D-Dimer (ng/mL) | | | | | |
| Baseline | 0.34 | 0.08 | 0.65 | 0.22 | 0.16 |
| 1 Week | 1.80 | 0.15 | 0.97 | 0.18 | 0.17 |
| 1 Month | 2.38 | 0.24 | 0.71 | 0.20 | 0.20 |
| SGPT-ALT (IU/L) | | | | | |
| Baseline | 17.3 | 14.6 | 18.0 | 9.4 | 11.9 |
| 1 Week | 15.3 | 28.0 | 38.7 | 15.2 | 20.1 |
| 1 Month | 19.9 | 19.2 | 12.3 | 19.7 | 13.8 |
| SGOT-AST (IU/L) | | | | | |
| Baseline | 20.6 | 44.0 | 16.9 | 12.4 | 12.5 |
| 1 Week | 21.9 | 18.8 | 32.0 | 14.8 | 16.8 |
| 1 Month | 23.4 | 21.4 | 13.8 | 16.0 | 14.1 |
| Glycemia (mmol/L) | | | | | |
| Baseline | 9.28 | 4.71 | 10.14 | 6.36 | 3.93 |
| 1 Week | 8.49 | 4.17 | 7.34 | 5.36 | 4.07 |
| 1 Month | 6.83 | 4.50 | 5.89 | 5.26 | 3.99 |

TABLE 3-continued

| Creatinine (μmol/l) | | | | | |
|---|---|---|---|---|---|
| Baseline | 53 | 53 | 46 | 81 | 43 |
| 1 Week | 57 | 68 | 54 | 95 | 51 |
| 1 Month | 44 | 55 | 51 | 87 | 47 |
| Red-blood cells | | | | | |
| Baseline | 4.32 | 4.15 | 4.57 | 5.10 | 3.48 |
| 1 Week | 4.18 | 4.07 | 4.67 | 5.31 | 3.73 |
| 1 Month | 3.70 | 4.50 | 4.71 | 4.74 | 3.76 |
| Mean RBC volume | | | | | |
| Baseline | 92.7 | 96.5 | 83.6 | 88.0 | 89.1 |
| 1 Week | 92.5 | 97.7 | 83.3 | 88.8 | 89.9 |
| 1 Month | 92.7 | 96.5 | 83.6 | 86.7 | 89.1 |
| white-blood cells | | | | | |
| Baseline | 9.0 | 5.9 | 9.4 | 8.8 | 3.8 |
| 1 Week | 9.4 | 5.9 | 8.1 | 8.3 | 3.7 |
| 1 Month | 5.1 | 6.0 | 10.0 | 12.8 | 3.5 |
| granulocytes | | | | | |
| Baseline | 7.9 | 4.1 | 6.4 | 4.9 | 2.4 |
| 1 Week | 7.8 | 3.5 | 4.6 | 4.0 | 2.3 |
| 1 Month | 3.6 | 3.7 | 6.3 | 8.8 | 1.9 |
| lymphocytes | | | | | |
| Baseline | 0.7 | 1.3 | 2.2 | 3.0 | 0.9 |
| 1 Week | 1.1 | 1.7 | 2.8 | 3.4 | 1.0 |
| 1 Month | 1.0 | 1.6 | 3.0 | 2.8 | 1.3 |
| Monocytes | | | | | |
| Baseline | 0.3 | 0.3 | 0.4 | 0.5 | 0.1 |
| 1 Week | 0.3 | 0.3 | 0.3 | 0.6 | 0.2 |
| 1 Month | 0.3 | 0.3 | 0.4 | 0.7 | 0.3 |
| eosinophiles | | | | | |
| Baseline | 0.0 | 0.1 | 0.1 | 0.1 | 0.2 |
| 1 Week | 0.1 | 0.1 | 0.2 | 0.2 | 0.1 |
| 1 Month | 0.1 | 0.1 | 0.1 | 0.3 | 0.1 |
| basophiles | | | | | |
| Baseline | 0.0 | 0.0 | 0.0 | 0.0 | 0.0 |
| 1 Week | 0.0 | 0.0 | 0.0 | 0.0 | 0.0 |
| 1 Month | 0.0 | 0.0 | 0.1 | 0.1 | 0.0 |
| hemoglobin (Hb) in g/L | | | | | |
| Baseline | 138 | 140 | 134 | 163 | 109 |
| 1 Week | 131 | 139 | 138 | 167 | 120 |
| 1 Month | 119 | 148 | 138 | 142 | 116 |
| hematocrit (Hct) in % | | | | | |
| Baseline | 40.1 | 40.1 | 38.2 | 44.9 | 31.0 |
| 1 Week | 45.8 | 39.8 | 38.8 | 47.1 | 33.5 |
| 1 Month | 34.3 | 43.4 | 39.4 | 41.1 | 33.5 |
| CRP (mg/dL) | | | | | |
| Baseline | 6.34 | 0.99 | 6.42 | 0.49 | 0.96 |
| 1 Week | 11.10 | 0.48 | 0.64 | 0.44 | 0.16 |
| 1 Month | 0.64 | 0.40 | 0.65 | 5.44 | 0.74 |
| | PATIENT 6 | PATIENT 7 | PATIENT 8 | PATIENT 8 | PATIENT 10 |
| Gender | F | F | M | M | M |
| Age | 60 | 64 | 85 | 48 | 69 |
| Day(s) from stroke onset | 7 | 1 | 1 | 4 | 7 |
| On Aspirin? | N | N | Y | Y | Y |
| Other Treatment administered | NeuroAid ®, digoxine, isosorbide mononitide, nimodipine, phenytoin | NeuroAid ®, phenytoin sodium, nimodipine | NeuroAid ®, aspirin, ISMN | NeuroAid ®, aspirin, ISMN, amlodipine | NeuroAid ®, aspirin, ISMN, amlodipine |

TABLE 3-continued

| NHSS | | | | | |
|---|---|---|---|---|---|
| Baseline | 4 | 6 | 4 | 3 | 2 |
| 1 Week | 12 | 4 | 3 | 3 | 1 |
| 1 Month | 10 | 2 | 2 | 2 | 1 |
| Rankin score | | | | | |
| Baseline | 4 | 4 | 2 | 3 | 1 |
| 1 Week | 5 | 2 | 2 | 2 | 1 |
| 1 Month | 4 | 1 | 1 | 1 | 1 |
| PT (secs) | | | | | |
| Baseline | 11.3 | 13.3 | 13.9 | 12.1 | 12.6 |
| 1 Week | 11.5 | 12.8 | 13.9 | 12.0 | 11.6 |
| 1 Month | 11.2 | 11.9 | 12.2 | 12.4 | 12.6 |
| APTT (secs) | | | | | |
| Baseline | 27.9 | 29.3 | 33.5 | 30.3 | 30.7 |
| 1 Week | 30.8 | 34.3 | 33.2 | 32.1 | 29.7 |
| 1 Month | 24.9 | 29.8 | 30.2 | 34.7 | 30.7 |
| Fibrinogen dosage (g/L) | | | | | |
| Baseline | 6.92 | 2.52 | 4.02 | 3.29 | 3.60 |
| 1 Week | 3.42 | 4.78 | 3.01 | 3.09 | 3.77 |
| 1 Month | 6.18 | 3.11 | 3.27 | 3.69 | 3.67 |
| Platelet agregation | | | | | |
| Baseline | 53.3 | 57.83 | 69.55 | 66.29 | 53.90 |
| 1 Week | 48.51 | 37.53 | 54.97 | 45.68 | 50.37 |
| 1 Month | 63.37 | 51.27 | 51.93 | 45.98 | 41.07 |
| D-Dimer (ng/mL) | | | | | |
| Baseline | 0.5 | 0.20 | 0.30 | 0.20 | 0.10 |
| 1 Week | 5.2 | 0.22 | 0.30 | 0.10 | 0.18 |
| 1 Month | 0.3 | 0.22 | 0.10 | 0.18 | 0.22 |
| SGPT-ALT (IU/L) | | | | | |
| Baseline | 18.8 | 20.3 | 8.9 | 14.5 | 9.9 |
| 1 Week | 17 | 28.9 | 8.1 | 21.4 | 11.5 |
| 1 Month | 12 | 33.4 | 9.7 | 21.1 | 10.8 |
| SGOT-AST (IU/L) | | | | | |
| Baseline | 18.3 | 12.5 | 23.2 | 17.4 | 12.8 |
| 1 Week | 30.2 | 16.7 | 13.1 | 17.6 | 11.1 |
| 1 Month | 22.7 | 15.4 | 15.9 | 13.8 | 11.3 |
| Glycemia (mmol/L) | | | | | |
| Baseline | 6.34 | 4.38 | 4.60 | 4.51 | 5.03 |
| 1 Week | 5.45 | 3.59 | 4.44 | 4.23 | 5.07 |
| 1 Month | 6.4 | 3.53 | 5.24 | 4.05 | 4.78 |
| Creatinine (µmol/l) | | | | | |
| Baseline | 72 | 100 | 90 | 86 | 83 |
| 1 Week | 47 | 93 | 105 | 85 | 72 |
| 1 Month | 52 | 89 | 88 | 82 | 68 |
| Red-blood cells | | | | | |
| Baseline | 4.13 | 4.29 | 4.79 | 5.14 | 3.90 |
| 1 Week | 4.33 | 4.64 | 4.60 | 5.16 | 4.24 |
| 1 Month | 4.4 | 4.67 | 5.36 | 5.13 | 4.50 |
| Mean RBC volume | | | | | |
| Baseline | 89.6 | 92.0 | 85.6 | 89.7 | 99.2 |
| 1 Week | 89.2 | 91.4 | 85.2 | 91.7 | 97.9 |
| 1 Month | 88.4 | 92.1 | 83.2 | 86.9 | 100.0 |
| white-blood cells | | | | | |
| Baseline | 7.8 | 4.2 | 7.7 | 7.2 | 3.7 |
| 1 Week | 11.7 | 6.9 | 5.1 | 5.2 | 3.8 |
| 1 Month | 7.2 | 6.2 | 6.0 | 5.7 | 4.8 |

TABLE 3-continued

| | | | | | |
|---|---|---|---|---|---|
| granulocytes | | | | | |
| Baseline | 5.3 | 2.8 | 5.0 | 5.7 | 2.8 |
| 1 Week | 7.7 | 5.4 | 3.1 | 3.2 | 3.0 |
| 1 Month | 3.9 | 4.7 | 3.6 | 3.7 | 3.6 |
| lymphocytes | | | | | |
| Baseline | 1.3 | 1.0 | 1.6 | 1.3 | 0.7 |
| 1 Week | 2.9 | 0.9 | 1.8 | 1.7 | 0.7 |
| 1 Month | 2.8 | 1.3 | 2.1 | 1.6 | 1.0 |
| Monocytes | | | | | |
| Baseline | 0.5 | 0.2 | 0.6 | 0.2 | 0.2 |
| 1 Week | 0.6 | 0.3 | 0.2 | 0.3 | 0.1 |
| 1 Month | 0.5 | 0.2 | 0.3 | 0.4 | 0.2 |
| eosinophiles | | | | | |
| Baseline | 0.1 | 0.4 | 0.2 | 0.1 | 0.1 |
| 1 Week | 0.1 | 0.1 | 0.2 | 0.1 | 0.1 |
| 1 Month | 0.1 | 0.1 | 0.2 | 0.1 | 0.1 |
| basophiles | | | | | |
| Baseline | 0.1 | 0.1 | 0.0 | 0.1 | 0.1 |
| 1 Week | 0.0 | 0.1 | 0.0 | 0.1 | 0.1 |
| 1 Month | 0.0 | 0.1 | 0.0 | 0.1 | 0.1 |
| hemoglobin (Hb) in g/L | | | | | |
| Baseline | 141 | 130 | 137 | 162 | 132 |
| 1 Week | 147 | 132 | 137 | 161 | 146 |
| 1 Month | 153 | 133 | 162 | 157 | 158 |
| hematocrit (Hct) in % | | | | | |
| Baseline | 39.5 | 37 | 41.0 | 46.1 | 38.7 |
| 1 Week | 42.4 | 38.7 | 39.2 | 47.3 | 41.5 |
| 1 Month | 43.0 | 38.9 | 44.6 | 44.6 | 45.0 |
| CRP (mg/dL) | | | | | |
| Baseline | 0.14 | 3.53 | 2.17 | 0.69 | 0.17 |
| 1 Week | 3.73 | 2.1 | 0.35 | 0.13 | 0.10 |
| 1 Month | 1.10 | 1.88 | 0.10 | 0.38 | 0.10 |

TABLE 4

| SUMMARY | MEAN | SD− | SD+ | SD |
|---|---|---|---|---|
| Gender | F = 5 | M = 4 | | |
| Age | 65.11 | 53.24 | 76.98 | 11.87 |
| Day(s) from stroke onset | 3.33 | 0.94 | 5.73 | 2.40 |
| On Aspirin? | Y = 5 | N = 4 | | |
| Other Treatment administered | | | | |
| NIHSS | | | | |
| Baseline | 7.11 | 0.86 | 13.36 | 6.25 |
| 1 Week | 4.89 | −0.17 | 9.95 | 5.06 |
| 1 Month | 4.11 | −0.37 | 8.60 | 4.48 |
| Rankin score | | | | |
| Baseline | 3.11 | 1.57 | 4.65 | 1.54 |
| 1 Week | 2.22 | 0.83 | 3.62 | 1.39 |
| 1 Month | 1.78 | 0.21 | 3.34 | 1.56 |
| PT (secs) | | | | |
| Baseline | 13.04 | 12.17 | 13.92 | 0.88 |
| 1 Week | 12.50 | 11.41 | 13.59 | 1.09 |
| 1 Month | 12.41 | 11.64 | 13.18 | 0.77 |
| APTT (secs) | | | | |
| Baseline | 30.96 | 28.70 | 33.21 | 2.26 |
| 1 Week | 32.10 | 29.17 | 35.03 | 2.93 |
| 1 Month | 30.68 | 28.87 | 32.48 | 1.80 |
| Fibrinogen dosage (g/L) | | | | |
| Baseline | 4.10 | 2.97 | 5.23 | 1.13 |
| 1 Week | 4.03 | 2.81 | 5.25 | 1.22 |
| 1 Month | 4.06 | 2.95 | 5.18 | 1.11 |
| Platelet agregation | | | | |
| Baseline | 63.61 | 54.67 | 72.55 | 8.94 |
| 1 Week | 52.31 | 40.68 | 63.94 | 11.63 |
| 1 Month | 48.44 | 36.31 | 60.58 | 12.14 |
| D-Dimer (ng/mL) | | | | |
| Baseline | 0.25 | 0.08 | 0.42 | 0.17 |
| 1 Week | 0.45 | −0.12 | 1.02 | 0.57 |
| 1 Month | 0.49 | −0.23 | 1.22 | 0.73 |
| SGPT - ALT (IU/L) | | | | |
| Baseline | 13.87 | 9.75 | 17.98 | 4.11 |
| 1 Week | 20.80 | 11.13 | 30.47 | 9.67 |
| 1 Month | 17.77 | 10.48 | 25.06 | 7.29 |
| SGOT - AST (IU/L) | | | | |
| Baseline | 19.14 | 9.03 | 29.26 | 10.11 |
| 1 Week | 18.09 | 12.00 | 24.18 | 6.09 |
| 1 Month | 16.12 | 12.26 | 19.99 | 3.87 |
| Glycemia (mmol/L) | | | | |
| Baseline | 5.88 | 3.60 | 8.16 | 2.28 |
| 1 Week | 5.21 | 3.44 | 6.98 | 1.77 |
| 1 Month | 4.91 | 3.81 | 6.02 | 1.10 |

TABLE 4-continued

| SUMMARY | MEAN | SD− | SD+ | SD |
|---|---|---|---|---|
| Creatinine (µmol/l) | | | | |
| Baseline | 70.56 | 48.97 | 92.14 | 21.58 |
| 1 Week | 75.56 | 55.81 | 95.30 | 19.75 |
| 1 Month | 67.89 | 48.94 | 86.84 | 18.95 |
| Red-blood cells | | | | |
| Baseline | 4.42 | 3.87 | 4.96 | 0.55 |
| 1 Week | 4.51 | 4.00 | 5.02 | 0.51 |
| 1 Month | 4.56 | 4.01 | 5.11 | 0.55 |
| Mean RBC volume | | | | |
| Baseline | 90.71 | 85.73 | 95.70 | 4.99 |
| 1 Week | 90.93 | 86.00 | 95.86 | 4.93 |
| 1 Month | 90.09 | 84.36 | 95.82 | 5.73 |
| white-blood cells | | | | |
| Baseline | 6.63 | 4.33 | 8.94 | 2.30 |
| 1 Week | 5.88 | 4.10 | 7.65 | 1.77 |
| 1 Month | 6.68 | 3.79 | 9.57 | 2.89 |
| granulocytes | | | | |
| Baseline | 4.67 | 2.83 | 6.51 | 1.84 |
| 1 Week | 4.10 | 2.43 | 5.77 | 1.67 |
| 1 Month | 4.43 | 2.43 | 6.44 | 2.01 |
| lymphocytes | | | | |
| Baseline | 1.41 | 0.65 | 2.17 | 0.76 |
| 1 Week | 1.68 | 0.77 | 2.59 | 0.91 |
| 1 Month | 1.74 | 1.01 | 2.48 | 0.74 |
| monocytes | | | | |
| Baseline | 0.31 | 0.15 | 0.47 | 0.16 |
| 1 Week | 0.29 | 0.15 | 0.43 | 0.14 |
| 1 Month | 0.34 | 0.19 | 0.50 | 0.15 |
| eosinophiles | | | | |
| Baseline | 0.11 | 0.05 | 0.17 | 0.06 |
| 1 Week | 0.13 | 0.08 | 0.18 | 0.05 |
| 1 Month | 0.13 | 0.06 | 0.20 | 0.07 |
| basophiles | | | | |
| Baseline | 0.03 | −0.02 | 0.08 | 0.05 |
| 1 Week | 0.02 | −0.02 | 0.07 | 0.04 |
| 1 Month | 0.04 | −0.01 | 0.10 | 0.05 |
| hemoglobin (Hb) in g/L | | | | |
| Baseline | 139.56 | 123.41 | 155.70 | 16.15 |
| 1 Week | 142.89 | 128.42 | 157.36 | 14.47 |
| 1 Month | 143.67 | 126.96 | 160.38 | 16.71 |
| hematocrit (Hct) in % | | | | |
| Baseline | 39.96 | 35.65 | 44.26 | 4.31 |
| 1 Week | 41.71 | 37.19 | 46.23 | 4.52 |
| 1 Month | 40.99 | 36.58 | 45.40 | 4.41 |
| CRP (mg/dL) | | | | |
| Baseline | 2.04 | −0.49 | 4.57 | 2.53 |
| 1 Week | 1.90 | −1.73 | 5.54 | 3.63 |
| 1 Month | 1.06 | −0.61 | 2.73 | 1.67 |

Example 7

Effect of NeuroAid® on Specific Potassium Channels

NeuroAid® powder was dissolved in distilled water at a concentration of 1 µg/ml. After 30 minutes infusion, the liquid was filtered on a 0.22 µm filter.

Cos-7 cells, cultured in Dulbecco's Modified Eagle Medium (DMEM; Gibco, Invitrogen, San Diego, Calif.) supplemented with 10% fetal bovine serum (Perbio, Thermo Fisher Scientific Inc., Waltham, Mass.), 100 U/ml penicillin and 100 µg/ml streptomycin (Gibco, Invitrogen, San Diego, Calif.) in a humidified incubator with 5% $CO_2$ at 37° C., were used for electrophysiological procedures. Cells were transfected using DEAE-Dextran (Sigma-Aldrich Corporation, St-Louis, Mo.) with 0.5 µg of TREK 1 or TREK 2 cloned in pIRES-EGFP plasmid (Clontech Palo Alto, Calif.) expressing the green fluorescent protein.

Recordings were realised 48 hours after transfection. For electrophysiological recordings, the internal solution contained 155 mM KCl, 3 mM $MgCl_2$, 5 mM EGTA and 10 mM HEPES (Sigma-Aldrich Corporation, St-Louis, Mo.) at pH 7.2 with KOH and the external solution contained 150 mM NaCl, 5 mM KCl, 3 mM $MgCl_2$, 1 mM $CaCl_2$ and 10 mM HEPES at pH 7.4 with NaOH. Effects of NeuroAid® on TREK currents were measured on whole-cell currents, elicited by voltage ramps (from −100 mV to +100 mV, 1.5 seconds in duration) before and during application of NeuroAid® (5 minutes). TREK 1 and TREK 2 currents were not different before and after 5 minutes of NeuroAid® application, comparing with control cells transfected with EGFP only.

The results show that NeuroAid® does not have any effect on potassium channels TREK-1. Hence, the results suggest that agents that activate potassium channels TREK-1 and NeuroAid® have different mechanisms and different targets. Accordingly, it may be beneficial to combine agents that activate potassium channels TREK-1 with NeuroAid® to enhance the neuroprotective effect of NeuroAid®.

It will be understood that the invention has been described by way of example only and modifications may be made whilst remaining within the scope and spirit of the invention.

The invention claimed is:

1. A product comprising a Chinese medicament comprising:
    (a) Chinese Angelica root (Radix *angelicae sinensis*; Dan-Gui); and
    (b) Membranous Milkvetch root (Radix astragali root; Huang Qi); rhizome of *Ligusticum chuanxionq* (Chuan Xiong); and Radix polygalae root (Yuan Zhi).

2. The product of claim 1 further comprising:
    (c) an agent used in Western medicine for treatment of cerebral stroke, heart attack, a neurodegenerative disease, brain trauma, nervous system trauma or a condition related to neuroplasticity.

3. A product comprising:
    (a) Chinese Angelica root (Radix *angelicae sinensis*; Dan-Gui);
    (b) Membranous Milkvetch root (Radix astragali root; Huang Qi); rhizome of *Ligusticum chuanxionq* (Chuan Xiong); and Radix polygalae root (Yuan Zhi); and
    (c) an agent used in Western medicine for the treatment of cerebral stroke, heart attack, a neurodegenerative disease, brain trauma, nervous system trauma or a condition related to neuroplasticity.

4. The product of claim 2 further comprising:
    (d) instructions for administration of (a), (b) and (c) to a patient.

5. The product of claim 1, wherein (a) and (b) are present in separate formulations.

6. The product of claim 1, wherein (a) and (b) are present in a single formulation.

7. The product of claim 3, wherein (a) and (b) are present in separate formulations.

8. The product of claim 3, wherein (a) and (b) are present in a single formulation.

9. The product of claim 5, wherein the product is a kit.

10. The product of claim 2, wherein the agent used in Western medicine is capable of activating potassium channel TREK-1.

11. The product of claim 10, wherein the agent used in Western medicine which is capable of activating potassium channels TREK-1 is a polyunsaturated fatty acid (PUFA), riluzole (Rilutek®), a lysophospholid (LPL), a Caffeic Acid ester or Xenon.

12. The product of claim 2, wherein the agent used in Western medicine is provided for simultaneous, separate or sequential use in the treatment of cerebral stroke, heart attack, a neurodegenerative disease, brain trauma, nervous system trauma or a condition related to neuroplasticity.

13. The product of claim 2, wherein the agent used in Western medicine is provided for simultaneous, separate or sequential use in treatment of a patient.

14. The product of claim 3, wherein the agent used in Western medicine is provided for simultaneous, separate or sequential use in treatment of a patient.

15. A method for treating a patient suffering from cerebral stroke or heart attack, comprising administering a therapeutically effective amount of the product of claim 1 to the patient.

16. The method of claim 15, wherein the method further comprises administering an agent used in Western medicine which is capable of activating potassium channel TREK-1 and which is administered simultaneously, separately or sequentially to the product.

17. The method of claim 15, wherein the Chinese Angelica root (Radix *angelicae sinensis*; DanGui); Membranous Milkvetch root (Radix astraqali root;
Huang Qi); rhizome of *Liqusticum chuanxionq* (Chuan Xiong); and Radix polygalae root (Yuan Zhi) are present in a single formulation.

18. A method for treating a patient suffering from cerebral stroke or heart attack, comprising administering to the patient a therapeutically effective amount of a product comprising:
(a) Chinese Angelica root (Radix *angelicae sinensis*; Dan-Gui):
(b) Membranous Milkvetch root (Radix astragali root; Huang Qi); rhizome of *Liqusticum chuanxionq* (Chuan Xiong); and Radix polygalae root (Yuan Zhi); and
(c) an agent used in Western medicine for the treatment of cerebral stroke or heart attack.

19. The method of claim 18, wherein the Chinese Angelica root (Radix *angelicae sinensis*; DanGui); Membranous Milkvetch root (Radix astragali root;
Huang Qi); rhizome of *Liqusticum chuanxionq* (Chuan Xiong); and Radix polygalae root (Yuan Zhi) are present in a single formulation.

20. The method of claim 19, wherein the agent used in Western medicine is administered simultaneously, separately or sequentially to the single formulation comprising the Chinese Angelica root (Radix *anqelicae sinensis*; DanGui); Membranous Milkvetch root (Radix astragali root; Huang Qi); rhizome of *Liqusticum chuanxionq* (Chuan Xionq); and Radix polygalae root (Yuan Zhi).

* * * * *